United States Patent
Xian et al.

(10) Patent No.: US 7,458,258 B2
(45) Date of Patent: Dec. 2, 2008

(54) METHODS AND APPARATUS FOR OIL COMPOSITION DETERMINATION

(75) Inventors: ChengGang Xian, Abu Dhabi (AE); Andrew Carnegie, Beijing (CN); ChengLi Dong, Sugar Land, TX (US); Oliver C. Mullins, Ridgefield, CT (US); Go Fujisawa, Kanagawa-Ken (JP)

(73) Assignee: Schlumberger Technology Corporation, Sugarland, TX (US)

( * ) Notice: Subject to any disclaimer, the term of this patent is extended or adjusted under 35 U.S.C. 154(b) by 364 days.

(21) Appl. No.: 11/303,695

(22) Filed: Dec. 16, 2005

(65) Prior Publication Data

US 2007/0137292 A1    Jun. 21, 2007

(51) Int. Cl.
*E21B 47/10* (2006.01)
(52) U.S. Cl. ................... 73/152.18; 73/152.01
(58) Field of Classification Search .............. 73/152.18, 73/152.01
See application file for complete search history.

(56) References Cited

U.S. PATENT DOCUMENTS

| | | | |
|---|---|---|---|
| 4,860,581 A | 8/1989 | Zimmerman et al. | |
| 4,936,139 A | 6/1990 | Zimmerman et al. | |
| 4,994,671 A | 2/1991 | Safinya et al. | |
| 5,939,717 A | 8/1999 | Mullins | |
| 6,476,384 B1 | 11/2002 | Mullins et al. | |
| 6,768,105 B2 | 4/2004 | Mullins et al. | |
| 6,956,204 B2 | 10/2005 | Dong et al. | |
| 7,081,615 B2 * | 7/2006 | Betancourt et al. | 250/255 |
| 2004/0000636 A1 | 1/2004 | Mullins et al. | |
| 2004/0069942 A1 | 4/2004 | Fujisawa et al. | |
| 2004/0219064 A1 | 11/2004 | Raghuraman et al. | |

OTHER PUBLICATIONS

A. Van Dusen, S. Williams, F.H. Fadnes and J. Irvine-Fortescue, Determination of Hydrocarbon Properties by Optical Analysis During Wireline Fluid Sampling, SPE 63252, Oct. 1-4, 2000.
C. Dong, O.C. Mullins, P.S. Hegeman, R. Teague, A. Kurkjian and H. Elshahawi, In-Situ Contamination Monitoring and GOR Measurement of Formation Fluid Samples, SPE 77899, Oct. 8-10, 2002.
B. Raghuraman, M. O'Keefe, K.O. Eriksen, L.A. Tau, O. Vikane, G. Gustavson and K. Indo, Real-Time Downhole Ph Measurement Using Optical Spectroscopy, SPE 93057, Feb. 2-4, 2005.

* cited by examiner

*Primary Examiner*—Hezron Williams
*Assistant Examiner*—Rodney T Frank
(74) *Attorney, Agent, or Firm*—Jeff Jiang; Hoffman Warnick (57) ABSTRACT

A method for determining properties of a formation fluid is provided and includes: obtaining fluid data related to Carbon-Hydrogen molecular bonds in C6+ from a fluid analyzer; and considering the fluid data to calculate mass fractions of hydrocarbon flowing through the fluid analyzer. The method further includes computing gas-oil-ratio of hydrocarbon based on the mass fractions of hydrocarbon. Another method for determining a gas-oil-ratio of a formation fluid includes: obtaining fluid data related to Carbon-Hydrogen molecular bonds in C6+ from a fluid analyzer; considering the fluid data to derive mass fractions of gas and oil; and computing gas-oil-ratio of hydrocarbon based on the derived mass fractions.

14 Claims, 8 Drawing Sheets

METHODS AND APPARATUS FOR OIL COMPOSITION DETERMINATION

FIELD OF THE INVENTION

The present invention relates generally to oilfield exploration and development. More particularly, the present invention relates to wireline downhole fluid analysis (DFA) and sampling using the measurement from a fluid analyzer.

BACKGROUND OF THE INVENTION

In order to evaluate the nature of underground formations surrounding a borehole, it is often desirable to obtain samples of formation fluids from various specific locations in a borehole. The analysis of a fluid sample provides information about the fluid's contents, density, viscosity, bubble point, and other important characteristics. This vital information is used for field planning decisions and for the optimization of upstream and downstream production facilities.

Typically, a fluid sample is obtained by lowering a fluid sampling tool into the well and withdrawing a fluid sample from an underground formation. One example of a sampling tool is the Modular Formation Dynamics Tester (MDT), which is a registered trademark of Schlumberger Technology Corporation, the assignee of this invention. Formation testing tools are disclosed in U.S. Pat. Nos. 4,860,581 and 4,936,139 to Zimmerman et. al, which are assigned to the assignee of the present invention Hydrocarbon fluids are now seen to be as complex as the rocks in which they accumulate. Compositional gradients, fluid density inversions, compartmentalization and viscosity variations all contribute to the complexities observed today in reservoir fluids. The accurate description of reservoir fluid is as essential as the accurate description of matrix for successful reservoir evaluation and development. DFA is a requirement to uncover these fluid complexities; indiscriminant sampling without DFA is too costly to be performed routinely. DFA allows discovery of the fluid and reservoir complexities, thereby enabling optimal completion, development and production scenarios.

Two fluid characteristics of particular importance are the gas-oil-ratio (GOR) and hydrocarbon compositions. The GOR is the ratio of the volume of the gaseous phase in the native formation fluids over the volume of liquid hydrocarbons at the standard conditions. The GOR is important in designing the upstream and downstream production facilities. For example, if the GOR is high, the surface facilities must be designed to handle a large amount of gas from the well. The measurement of hydrocarbon compositional gradients within a given reservoir compartment or determination of reservoir compartments by identification of differences in fluid compositions and GOR would most likely not occur for other reasons.

The traditional application for MDT fluid analyzers was to monitor filtrate contamination while sampling. After formation fluid is withdrawn from the formation, the fluid passes through a fluid analyzer before it is pumped out of the tool and into the borehole. The fluid analyzer analyzes the sample fluid to determine the level of mud filtrate contamination. Newly developed applications for MDT fluid analyzers as a part of DFA are to measure fluid properties in real-time at reservoir conditions such as GOR, and hydrocarbon compositions together with quantified contamination and cleanup predictions with or without sampling.

One type of fluid analyzer used in a formation testing tool is an optical sensor, which measures the optical density ("OD") of the sample fluid at several different wavelengths. There are two types of absorption mechanism that contribute to the measured OD of a fluid sample: electron excitation and molecular vibration mode excitation. Absorption by electron excitation occurs when the energy of incident light is transferred to excite delocalized pi electrons to anti-bonding states. This energy level typically corresponds to visible to near-infrared range and gives a shade of color as a result. Molecular vibration absorption is the absorption of a particular frequency of light due to resonance of the chemical bonds in a molecule, and occurs only at specific wavelengths for specific materials. For any given molecule, the wavelength at which vibration absorption occurs is related to the type of chemical bonds and the molecular structure.

One type of such optical sensor is the Optical Fluid Analyzer ("OFA"), which is a trademark of Schlumberger. The OFA, which is a fluid analysis module as found in the MDT mentioned above, determines the identity of the fluids in the MDT flow stream and quantifies the oil and water content. In particular, U.S. Pat. No. 4,994,671 to Safinya, et al. (incorporated herein by reference) describes a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analyzed by directing the light at the fluids, detecting the spectrum of the transmitted and/or backscattered light, and processing the information accordingly (and preferably based on the information in the data base relating to different spectra), in order to quantify the amount of water and oil in the fluid. Thus, the formation oil can be properly analyzed and quantified by type.

Another type of optical sensor is called the Live Fluid Analyzer ("LFA"), which is a trademark of Schlumberger. The LFA has as same capabilities as OFA to quantify the amount of water and oil in the fluid. The LFA is different from the OFA because the LFA includes a methane channel at the wavelength of a "methane peak" and an oil channel at the wavelength of an "oil peak." A "methane peak" is a molecular vibration absorption peak of methane, whose wavelength corresponds to the resonance of the CH bond in a methane molecule; one methane molecular vibration absorption peak is at a wavelength of about 1,670 nm. The molecular vibration absorption occurs independently of the color of the fluid and independently of whether the methane is in the gas phase or dissolved in the formation fluid. Similarly, an "oil peak" is a molecular vibration absorption peak of oil, whose wavelength corresponds to the resonance of the combination of —$CH_2$ and —$CH_3$ groups in an oil molecule. One oil peak is at a wavelength of about 1,720 nm. GOR can be derived from the ratio of the amplitudes of the "methane peak" and the "oil peak."

Another type of optical sensor is called the Advanced Fluid Analyzer ("AFA"), which is a trademark of Schlumberger. The AFA has as same capabilities as OFA and LFA to quantify the amount of water and oil in the fluid, which has a U.S. Pat. Publication No. US20040219064 to Raghuraman et al. and is incorporated herein by reference. The AFA also has as same capability as LFA to determine GOR as LFA. The AFA is different from LFA because AFA has upgraded two OD channels in visible regime as "acid channel" and "base channel" to focus on the optical spectra of pH-sensitive dyes in solutions. The acid OD is measured at 445 nm and the base OD is measured at 570 nm. In addition, there is also a reference channel, 815 nm, which has zero response to water and the pH-sensitive dyes. To make a pH measurement, the pH sensitive dye is injected from a dye chamber into the flowline through which the formation fluid is being pumped. The OD ratio between the "acid" and the "base" is then determined from the optical spectra of this dye-water mixture as it flows past the AFA analyzer, further to derive the pH of formation fluid.

SUMMARY OF THE INVENTION

It is an object of the invention to provide alternative methods and apparatus for oil composition determination.

It is another object of the invention to reveal the in-situ composition analysis capability of the fluid analyzer OFA, LFA and AFA.

It is another object of the invention to provide methods and apparatus for oil composition determination without measurement of the absorptions by the molecular bonds of methane.

It is a further object of the invention to provide methods and apparatus for oil composition determination using a measurement of the absorption from the Carbon-Hydrogen molecular bonds in C6+.

It is still another object of the invention to determine C1-C5 and C6+ mass fractions of a liquid hydrocarbon flowing through a fluid analyzer.

It is still another object of the invention to determine C1, C2-C5, and C6+ mass fractions of a liquid hydrocarbon flowing through the fluid analyzer.

It is still another object of the invention to determine the gas oil ratio (GOR) of a liquid hydrocarbon flowing through the fluid analyzer.

It is still another object of the invention to quality check GOR determined by other methods.

In accord with the objects of the invention which will be discussed in more detail below, a method for determining properties of a formation fluid is provided and includes: obtaining fluid data related to Carbon-Hydrogen molecular bonds in C6+ from a fluid analyzer; and considering the fluid data to calculate mass fractions of hydrocarbon flowing through the fluid analyzer. The method further includes computing gas-oil-ratio of hydrocarbon based on the mass fractions of hydrocarbon.

In a preferred embodiment of the invention, another method for determining a gas-oil-ratio of a formation fluid includes: obtaining fluid data related to Carbon-Hydrogen molecular bonds in C6+ from a fluid analyzer; considering the fluid data to derive mass fractions of gas and oil; and computing gas-oil-ratio of hydrocarbon based on the derived mass fractions.

Additional objects and advantages of the invention will become apparent to those skilled in the art upon reference to the detailed description taken in conjunction with the provided figures.

BRIEF DESCRIPTION OF THE DRAWINGS

The present invention is illustrated by way of example and not intended to be limited by the figures of the accompanying drawings in which like references indicate similar elements and in which.

DETAILED DESCRIPTION OF THE INVENTION

Figure 1:
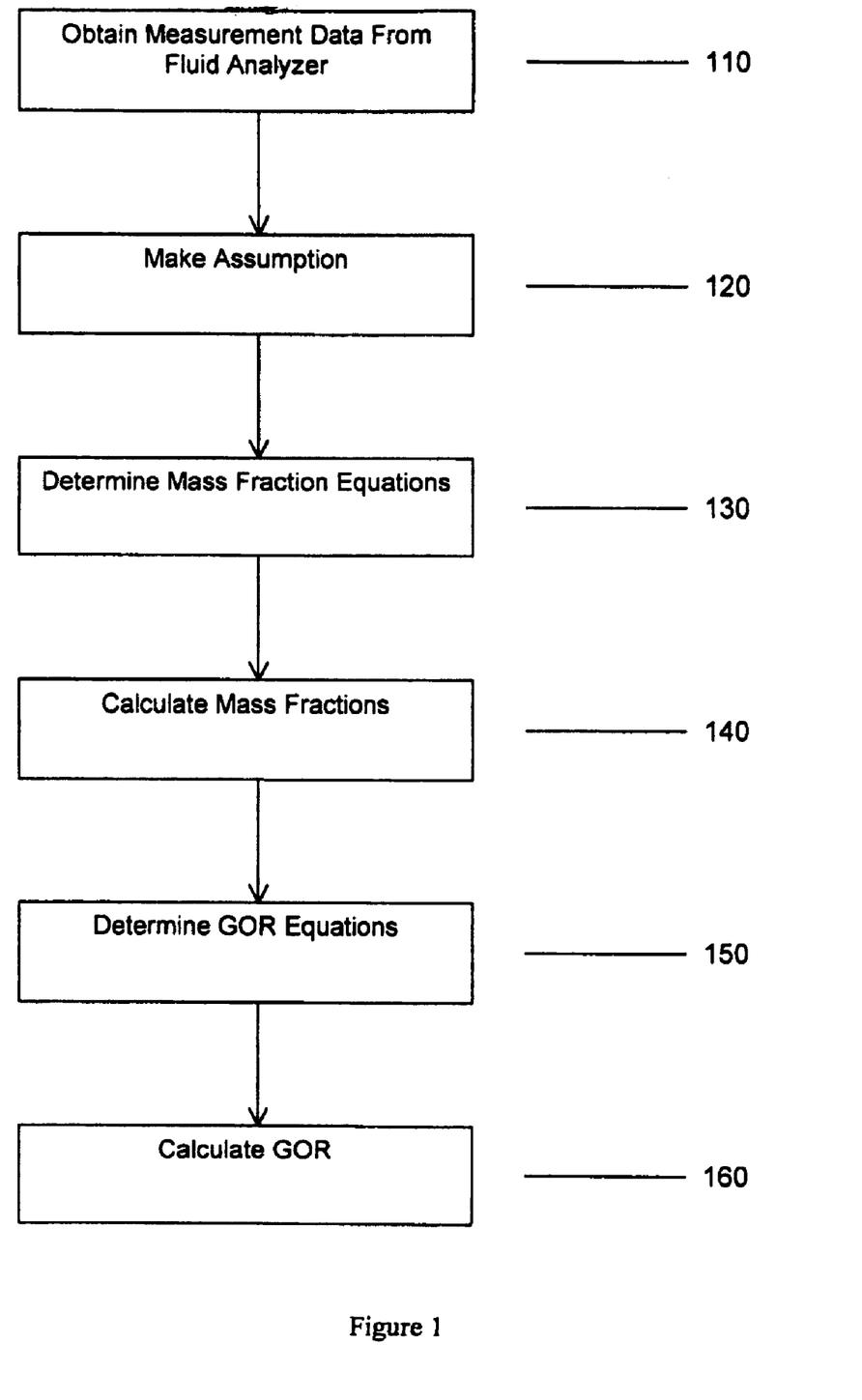
FIG. 1 is a flowchart showing steps associated with the present method and apparatus.

FIG. 1 is a flowchart showing steps associated with the present method and apparatus. In certain embodiments, the present invention relates to methods for downhole fluid analysis using the Optical Fluid Analyzer (OFA), Live Fluid Analyzer (LFA), and Advanced Fluid Analyzer (AFA), which are trademarks of Schlumberger. The method uses the OFA, LFA and/or AFA measurements to calculate mass fractions of hydrocarbon flowing through the fluid analyzer and compute gas-oil-ratio of hydrocarbon based on the mass fractions of hydrocarbon.

In Step 110, when the formation fluid passes through a fluid analyzer, e.g. OFA, LFA and/or AFA, the fluid analyzer can measure the fluid information such as the optical density of the sample fluid at several different wavelengths. In one embodiment, the fluid analyzer measures Near Infrared (NIR) optical densities along wavelengths affected by the Carbon-Hydrogen bonds of hydrocarbon molecules which contain 6 or more carbon atoms (C6+). In addition, the fluid analyzer can also measure Oxygen-Hydrogen bonds of water molecules.

In Step 120, certain assumptions are made in case of different situations. In one embodiment, it is assumed that the total hydrocarbon fraction from the fluid analyzer at a specific time is 1.0 in case of the absence of water in the flowline. In such case, the Step 130 determines equations for calculating mass fractions of hydrocarbon flowing through the fluid analyzer. Specifically, the mass fractions of C1-C5 and C6+ can be calculated by equations (1) and (2) below:

$$C6+ = XFA\_OILF \quad (1)$$

$$C1-C5 = 1 - C6+ \quad (2)$$

where C6+ and C1-C5 are mass fractions of liquid hydrocarbon respectively; XFA represents a certain type of fluid analyzer such as OFA, LFA or AFA; and XFA_OILF is the directly measured oil fraction from the fluid analyzer.

In another embodiment, it is assumed that the total fraction of hydrocarbon/water mixture at a specific time is 1.0 in case of oil and water mixing flow in the flowline. In such case, the Step 130 determines equations for calculating mass fractions of C1-C5 and C6+ flowing through the fluid analyzer by equations (3), (4) and (5) below:

$$XFA\_GASF=1-XFA\_OILF-XFA\_WATF \tag{3}$$

$$C6+=XFA\_OILF/(XFA\_OILF+XFA\_GASF) \tag{4}$$

$$C1-C5=XFA\_GASF/(XFA\_OILF+XFA\_GASF) \tag{5}$$

where C6+ and C1-C5 are mass fractions of liquid hydrocarbon respectively; XFA represents a certain type of fluid analyzer such as OFA, LFA or AFA; XFA_OILF and XFA_WATF are the directly measured oil and water fractions from the fluid analyzer.

Therefore, mass fractions of C1-C5 and C6+ can be easily calculated according to equations (1) to (5) in Step 140. In addition to that, the present method derives mass fractions C1-C5 and C6+ by equations (1) to (5), which avoids the need for a measurement of the absorptions by the molecular bonds of methane, and instead only uses a measurement of the absorption from the Carbon-Hydrogen molecular bonds in C6+.

Figure 2:
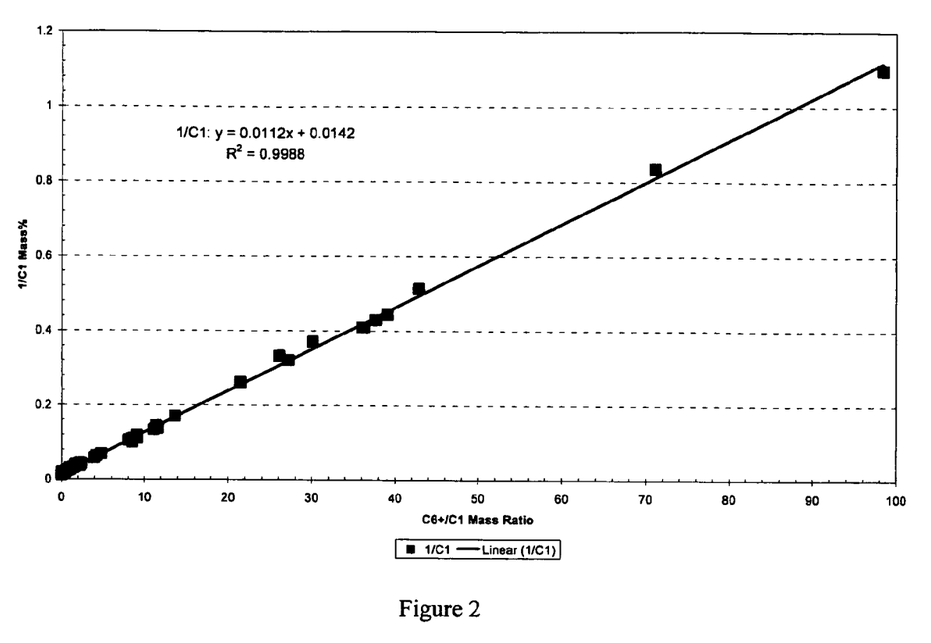
FIG. 2 is a diagram of linear fit of a first correlation used to illustrate the method.

The current method can also calculate C1, C2-C5, and C6+ mass fractions flowing through the fluid analyzer by deriving a correlation related to the mass fractions of C1-C5 and C6+. In one embodiment, the mass fractions of C1, C2-C5, and C6+ can be calculated by equations (6) to (11) below, which is illustrated in FIG. 2 (Linear Correlation) and FIG. 3 (Log-log Correlation) respectively:

Linear Correlation $$Y=aX+b \tag{6}$$

where, $$X=C6+/C1 \tag{7}$$

$$Y=1/C1 \tag{8}$$

In one embodiment, the recommended values of constants a, and b of equation (6) are 0.0112 and 0.0142 respectively, with $R^2=0.9988$.

and

Figure 3:
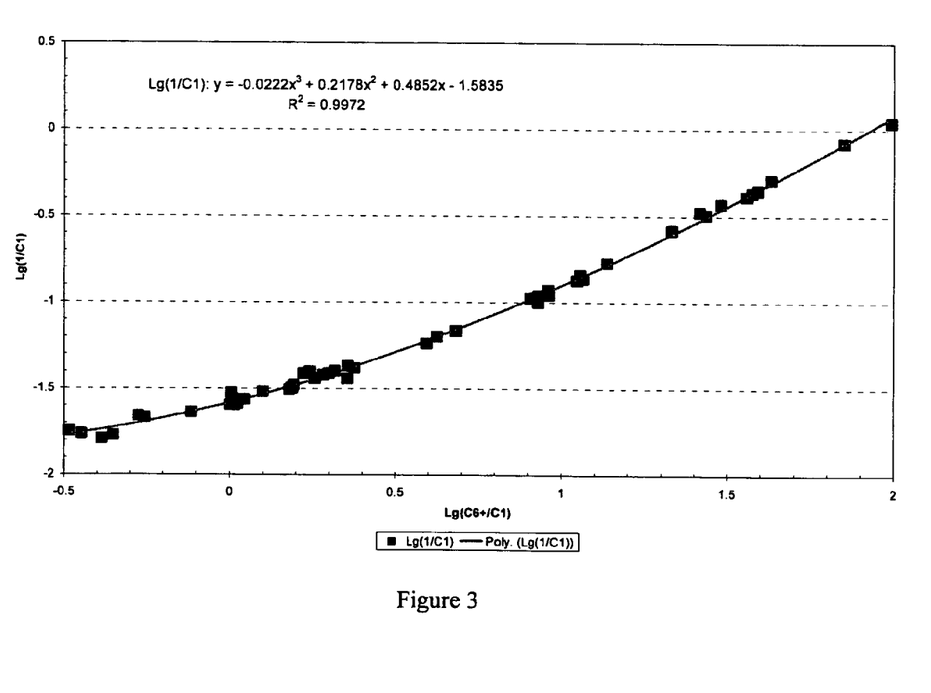
FIG. 3 is a diagram of log-log fit of the first correlation used to illustrate the method.

Log-log Correlation $$Y=aX^3+bX^2+cX+d \tag{9}$$

where, $$X=\text{Log }10(C6+/C1) \tag{10}$$

$$Y=\text{Log }10(1/C1) \tag{11}$$

In one embodiment, the recommended values of constants a, b, c, and d of equation (9) are −0.0222, 0.2178, 0.4852, and −1.5835, with $R^2=0.9972$.

Figure 4:
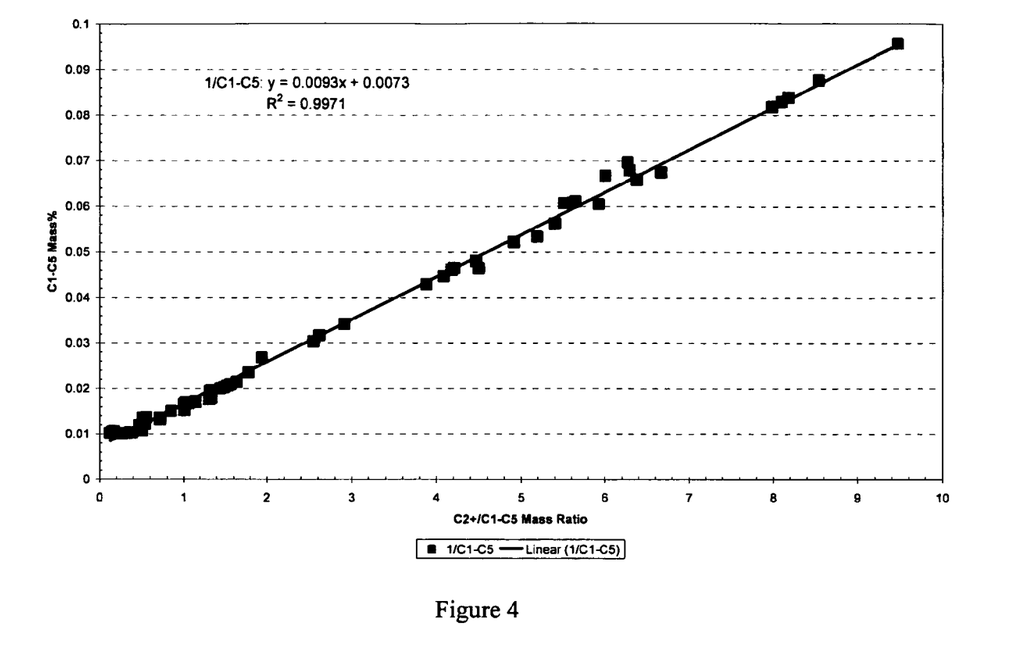
FIG. 4 is a diagram of linear fit of a second correlation used to illustrate the method.
Figure 5:
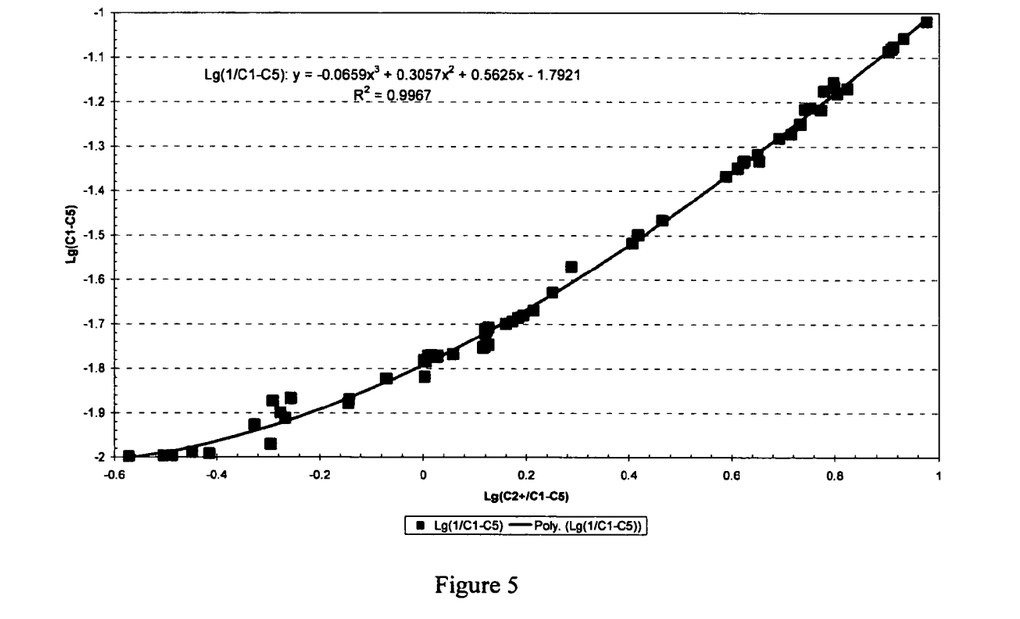
FIG. 5 is a diagram of log-log fit of the second correlation used to illustrate the method.

In another embodiment, the mass fractions of C1, C2-C5, and C6+ can be calculated by equations (12) to (17) below, which is illustrated in FIG. 4 (Linear Correlation) and FIG. 5 (Log-log Correlation) respectively:

Linear Correlation $$Y=aX+b \tag{12}$$

where, $$X=C2+/C1-C5 \tag{13}$$

$$Y=1/C1-C5 \tag{14}$$

In one embodiment, the recommended values of constants a, and b of equation (12) are 0.0093 and 0.0073 respectively, with $R^2=0.9971$.

and

Log-log Correlation $$Y=aX^3+bX^2+cX+d \tag{15}$$

where, $$X=\text{Log }10(C2+/C1-C5) \tag{16}$$

$$Y=\text{Log }10(1/C1-C5) \tag{17}$$

In one embodiment, the recommended values of constants a, b, c, and d of equation (15) are −0.0659, 0.3057, 0.5625, and −1.7921, with $R^2=0.9967$.

Therefore, within Step 140, C1, C2-C5, and C6+ mass fractions can be computed immediately by using the correlations above after the determination of C1-C5, and C6+ mass fractions of liquid hydrocarbon from a fluid analyzer. It must be pointed out that the correlations are generally applicable for all kinds of hydrocarbon such as condensate and gas, including liquid hydrocarbon. In addition to that, the present method derives mass fractions C1, C2-C5 and C6+ by equations (1) to (17), which avoid the need for a measurement of the absorptions by the molecular bonds of methane, and instead only use a measurement of the absorption from the Carbon-Hydrogen molecular bonds in C6+.

After C1, C2-C5, and C6+ mass fractions are calculated, in Step 150, gas-oil-ratio (GOR) of hydrocarbon can be calculated by equations (18) and (19) below, as disclosed by Schlumberger U.S. Pat. No. 6,956,204 to Dong et al. and Schlumberger U.S. Pat. No. 6,768,105 to Mullins et al., which are incorporated herein by reference.

$$GOR=8930*C1/(C6+-0.193*C1)scf/stb \tag{18}$$

$$GOR=5.61*1776*(0.625*C1+0.25*C2-C5)/C6+ \\ scf/stb \tag{19}$$

where, C1, C2-C5, and C6+ are mass fractions of hydrocarbon, scf represents standard cubic feet, and stb represents standard barrel.

Therefore, in Step 160, GOR of hydrocarbon can be decided according to equations (18) and (19). In addition to that, the present method derives GOR by equations (1) to (19), which avoid the need for a measurement of the absorptions by the molecular bonds of methane, and instead only use a measurement of the absorption from the Carbon-Hydrogen molecular bonds in C6+.

It shall be noted that, in one or more embodiments of the invention, the methods described above and explained in equations (1) to (19) use the following assumption: the non-water fluid that is in the flow line has negligible amounts molecular bonds that are not Carbon-Hydrogen, where compounds that contain such negligible amounts molecular bonds are N2, H2S, CO2 and asphaltenes.

The development of the two correlations (equations (6) to (17)) has been done by the following procedures:

1) A large number of reservoir hydrocarbon samples are collected from diverse sources. All hydrocarbon samples have detailed PVT analysis at least up to C7+.
2) Mass fractions of all components (i.e, C1, C2, C3, . . . ) are derived from mole fractions, which were generally obtained from PVT analysis in laboratories.
3) C1, C2-C5 and C6+ mass fractions of hydrocarbon components are calculated. Non-hydrocarbon components are excluded.

4) The possible correlations linking C1, C2-C5 and C6+ mass fractions and their combinations are investigated by fitting the PVT samples.

5) The correlations with $R^2>99\%$ are validated against other randomly chosen PVT samples.

Specifically, a large number of reservoir fluid samples are collected into a PVT database from diverse sources, which covered black oil, volatile oil, condensate, wet gas and dry gas. The samples are from all over the world including Gulf of Mexico (GOM), South America, North Sea, Africa, and Middle East Asia (MEA). The samples were collected via different sampling methods such as downhole sampling via formation testers, downhole sampling via well testing or production logging/testing, surface sampling via well testing or production testing, recombined samples from well string or separators, and so on. Furthermore, different laboratories performed the PVT analysis of those reservoir fluid samples. Therefore, the samples should be representative, and they would likely follow the general trend also.

It should be pointed out that the coefficients of the correlations could be upgraded after the PVT database is upgraded. It is also possible to have different correlations to fit different types of hydrocarbons (i.e., black oil, volatile oil, condensate, wet gas and dry gas) respectively. Moreover, it is possible to have different correlations against different combinations of C1, C2-C5, and C6+ mass fractions, by using as same idea as the present invention. But the method outlined here should be generally applicable in all similar situations.

The present methods can be applied in the conventional fluid analyzers so that the fluid analyzers OFA/LFA/AFA can analyze the oil composition. In one embodiment, the fluid analyzer includes a sensor for measuring fluid data related to Carbon-Hydrogen molecular bonds in C6+; and a processor for calculating mass fractions of hydrocarbon flowing through the fluid analyzer based on the measured fluid data In addition, the sensor can also measure fluid data related to Oxygen-Hydrogen bonds of water molecules. Thus, the fluid analyzer can directly calculate the mass fractions of hydrocarbon, e.g. C1-C5 and C6+ mass fractions; C1, C2-C5, and C6+ mass fractions. The fluid analyzer can further compute gas-oil-ratio of hydrocarbon based on the mass fractions of hydrocarbon. In one embodiment, the sensor is the same one as included in the conventional fluid analyzers, e.g. OFA/LFA/AFA, which is part of a formation testing tool that is disclosed in Schlumberger U.S. Pat. No. 6,956,204 and is incorporated herein by reference.

Figure 6:
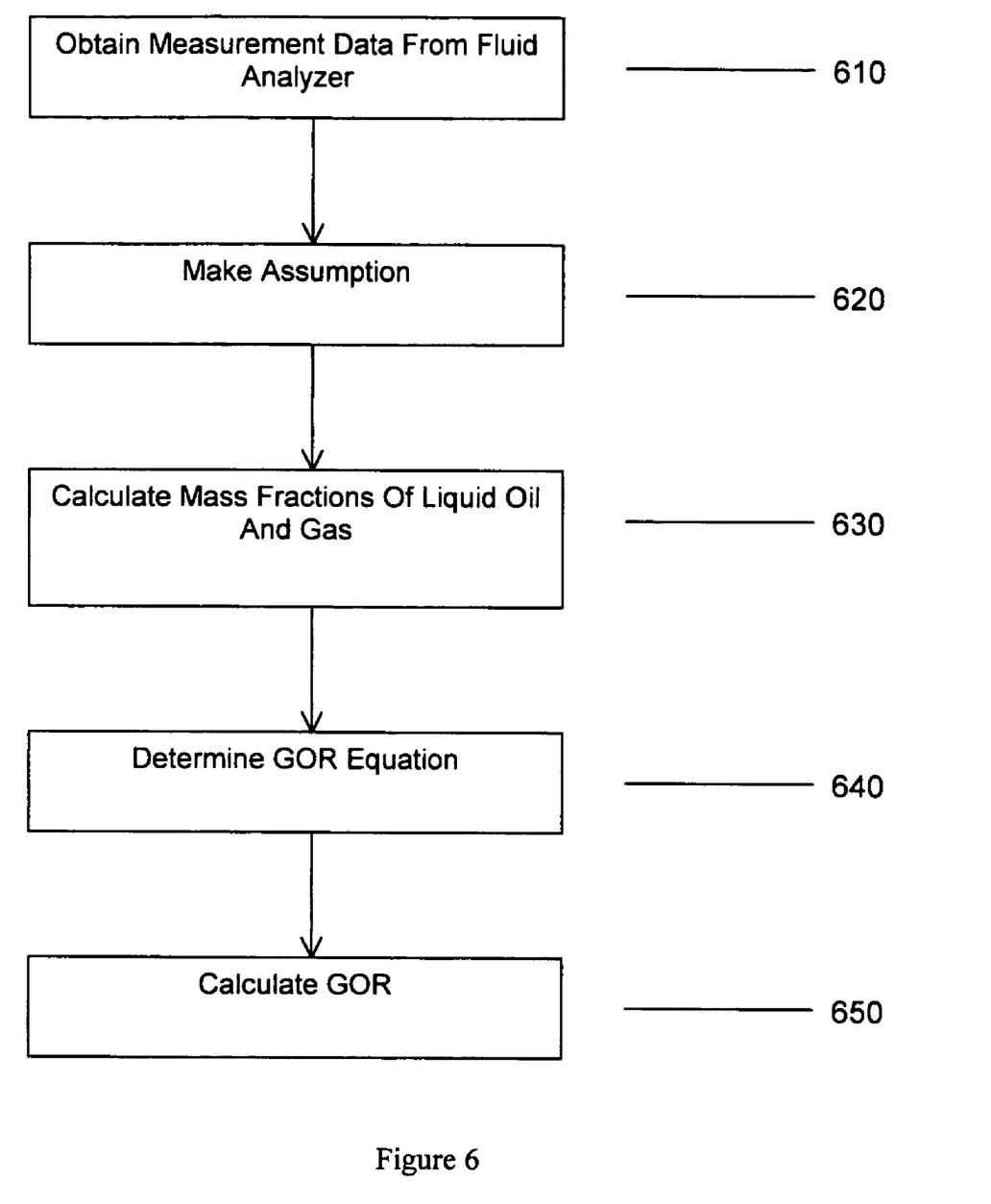
FIG. 6 is a flowchart showing steps associated with another method and apparatus for calculating gas oil ratio (GOR) of hydrocarbon.

FIG. 6 is a flowchart showing steps associated with another method and apparatus for calculating gas oil ratio (GOR) of hydrocarbon. In Step 610, when the formation fluid passes through a fluid analyzer, e.g. OFA, LFA and/or AFA, the fluid analyzer can measure the fluid information such as the optical density of the sample fluid at several different wavelengths. In one embodiment, the fluid analyzer measures Near Infrared (NIR) optical densities along wavelengths affected by the Carbon-Hydrogen molecular bonds in C6+. In addition, the fluid analyzer can also measure Oxygen-Hydrogen bonds of water molecules.

In Step 620, it is assumed that the non-water fluid that is in the flow line has negligible amounts molecular bonds that are not Carbon-Hydrogen, where compounds that contain such negligible amounts molecular bonds are N2, H2S, CO2 and asphaltenes. In Step 630, mass fractions of liquid oil (C6+) and gas (C1) in the flow line are calculated using equations (20) and (21) below based on the fluid analyzer measurements:

$$C1=(1-C6+-XFA\_{WATF})*gas\_reservoir\_density/(1-XFA\_{WATF}) \quad (20)$$

$$C6+=XFA\_OILF*Specific\_gravity\_reservoir\_oil/Specific\_gravity\_J261 \quad (21)$$

where XFA_OILF is the fraction of liquid in the hydrocarbon as measured by the fluid analyzer; XFA_WATF is the fraction of water hydrocarbon as measured by the fluid analyzer; Specific_gravity_reservoir_oil is the specific gravity of the liquid hydrocarbon when it is flashed at standard temperature and pressure (STP); Gas_reservoir_density (g/cc) is the density of the gas in the hydrocarbon at flow line conditions; and Specific_gravity_J261 is the specific gravity of the fluid which is used to calibrate the liquid oil response of the LFA and OFA (at surface Specific_gravity_J261 is 0.862).

After mass fractions of liquid oil (C6+) and gas (C1) in the flow line are determined, in Step 640, GOR can be calculated using equation (22) below based on the determined mass fractions of liquid oil (C6+) and gas (C1):

$$GOR=8930*C1/(C6+-0.193*C1) scf/stb \quad (22)$$

where C6+ and C1 are respectively the mass fractions of liquid oil and gas in the flow line; scf represents standard cubic feet, and stb represents standard barrel.

Therefore, in step 650, GOR of hydrocarbon can be decided according to equation (22).

The equation (22) above can be used to compute GOR from LFA/AFA measurements of Near Infrared (NIR) optical densities along wavelengths affected by the Carbon-Hydrogen bonds of methane (this compound will be denoted by the associated carbon number, C1), and by the Carbon-Hydrogen bonds of hydrocarbon molecules which contain 6 or more carbon atoms (these will be denoted by the associated carbon number, C6+), to determine the mass fractions of C1 and C6+ in a flow line of a formation tester, as disclosed by Schlumberger U.S. Pat. No. 6,476,384 to Mullins et al and Schlumberger U.S. Pat. No. 6,768,105 to Mullins et al, which are incorporated herein by reference. In addition to that, the present method derives mass fractions C1 and C6+ by equations (20) and (21), which avoid the need for a measurement of the absorptions by the molecular bonds of methane, and instead only use a measurement of the absorption from the Carbon-Hydrogen molecular bonds in C6+. It shall be noted that the present method assumes that the non-water fluid that is in the flow line has negligible amounts molecular bonds that are not Carbon-Hydrogen, where compounds that contain such negligible amounts molecular bonds are N2, H2S, CO2 and asphaltenes.

The parameters Specific_gravity_reservoir_oil, gas density may be determined as follows:

1) If available, from reports of lab analysis of the hydrocarbon. This type of input is useful when checking the conventionally determined LFA and/or AFA GOR; or
2) From the coloration of oil FCOL parameter as measured by the fluid analyzer. There are several correlations available between FCOL and Specific_gravity_reservoir_oil, gas density. Examples are disclosed in SPE 63252, which are incorporated herein by reference; or
3) From the value examining the equation: GSF=XFA_OILF (1−XFA_WATF). There are correlations between gsf and Specific_gravity_reservoir_oil. For example, the one immediately below is applicable to the UAE hydrocarbons:

```
If (gsf < 0.65 And gsf > 0.4) Then
    gas_reservoir_density = 0.3
    oil_specific_gravity = 0.79 / 0.862
If (gsf < 0.8 And gsf > 0.65) Then
    gas_reservoir_density = 0.28
    oil_specific_gravity = 0.79 / 0.862
If (gsf < 0.95 And gsf >= 0.8) Then
    gas_reservoir_density = 0.25
    oil_specific_gravity = 0.82 / 0.862
If (gsf < 1.1 And gsf >= 0.95) Then
    gas_reservoir_density = 0.3
    oil_specific_gravity = 0.89 / 0.862
```

Additionally, the parameter gas_reservoir_density, may be determined if the oil being examined sits below a gas cap, in which a pressure gradient vs. depth has been measured by a formation tester. This gradient gives the gas density.

The present methods can be applied in the conventional fluid analyzers so that the fluid analyzers OFA/LFA/AFA can analyze the oil composition and compute GOR. In one embodiment, the fluid analyzer includes a sensor for measuring fluid data related to Carbon-Hydrogen molecular bonds in C6+; and a processor for considering the measured fluid data to derive mass fractions of gas and oil and further to compute gas-oil-ratio of hydrocarbon based on the derived mass fractions.

Such methods and apparatus to calculate GOR are accurate comparing with other conventional methods thus can be used to provide an independent quality check on the GOR which is conventionally computed by the LFA and/or AFA (e.g. a downhole GOR computed from optical spectroscopy). For example, a check might be needed to determine whether the conventional LFA/AFA GOR is likely to more accurate than a GOR determined by lab analysis of samples, in the event that the two quantities have a significant disagreement. In addition, a check might be needed to determine what are the likely variations of measured GOR and the most probable measured GOR by LFA/AFA, in the event that the conventional LFA/AFA GORs from multiple measurements performed on the same oil have significant disagreements.

We now provide some experimental results of applying the present methods to calculate mass fractions of hydrocarbon and compute GOR of hydrocarbon. A few of case studies are provided, which yields further insights into the advantages of the present methods.

EXAMPLES OF APPLICATION OF THE PRESENT METHODS (1) LFA Example

Table 1 shows the excellent agreements between the LFA C6+ mass fractions computed from equations (1) to (2) and the PVT C6+ mass fractions from laboratory. Further, calculated C1, C2-C5, and C6+ mass fractions from five stations are listed in the table 2 and table 3. The overall agreements between calculated and PVT results are excellent.

TABLE 1

Comparison between measured C6+ mass fractions from LFA and PVT results

| Depth (ft) | LFA C6+ Mass Fraction | PVT C6+ |
|---|---|---|
| XX73.0 | 0.89 | 0.88073 |
| XX57.0 | 0.79 | 0.79178 |
| XX65.0 | 0.80 | 0.80852 |
| XX10.0 | 0.87 | 0.88301 |
| XX22.0 | 0.88 | 0.87757 |

TABLE 2

Comparison between calculated C1, C2-C5, and C6+ mass fractions and PVT results (Linear Fit)

| | C1 | | | C2-C5 | | | C6+ | | |
|---|---|---|---|---|---|---|---|---|---|
| Depth (ft) | Correlation 1 | Correlation 2 | PVT | Correlation 1 | Correlation 2 | PVT | Correlation 1 | Correlation 2 | PVT |
| XX73.0 | 0.002 | 0.011 | 0.024 | 0.108 | 0.099 | 0.095 | 0.890 | 0.890 | 0.881 |
| XX57.0 | 0.081 | 0.090 | 0.069 | 0.129 | 0.120 | 0.139 | 0.790 | 0.790 | 0.792 |
| XX65.0 | 0.073 | 0.082 | 0.059 | 0.127 | 0.118 | 0.132 | 0.800 | 0.800 | 0.809 |
| XX10.0 | 0.018 | 0.027 | 0.024 | 0.112 | 0.103 | 0.090 | 0.870 | 0.870 | 0.886 |
| XX22.0 | 0.010 | 0.019 | 0.023 | 0.110 | 0.101 | 0.099 | 0.880 | 0.880 | 0.878 |

TABLE 3

Comparison between calculated C1, C2-C5, and C6+ mass fractions and PVT results (Log-log Poly Fit)

| | C1 | | | C2-C5 | | | C6+ | | |
|---|---|---|---|---|---|---|---|---|---|
| Depth (ft) | Correlation 1 | Correlation 2 | PVT | Correlation 1 | Correlation 2 | PVT | Correlation 1 | Correlation 2 | PVT |
| XX73.0 | 0.026 | 0.027 | 0.024 | 0.084 | 0.083 | 0.095 | 0.890 | 0.890 | 0.881 |
| XX57.0 | 0.085 | 0.079 | 0.069 | 0.125 | 0.131 | 0.139 | 0.790 | 0.790 | 0.792 |
| XX65.0 | 0.795 | 0.072 | 0.059 | 0.120 | 0.128 | 0.132 | 0.800 | 0.800 | 0.809 |
| XX10.0 | 0.031 | 0.034 | 0.024 | 0.099 | 0.096 | 0.090 | 0.870 | 0.870 | 0.886 |
| XX22.0 | 0.025 | 0.030 | 0.023 | 0.095 | 0.090 | 0.099 | 0.880 | 0.880 | 0.878 |

(2) AFA Example

Figure 7:
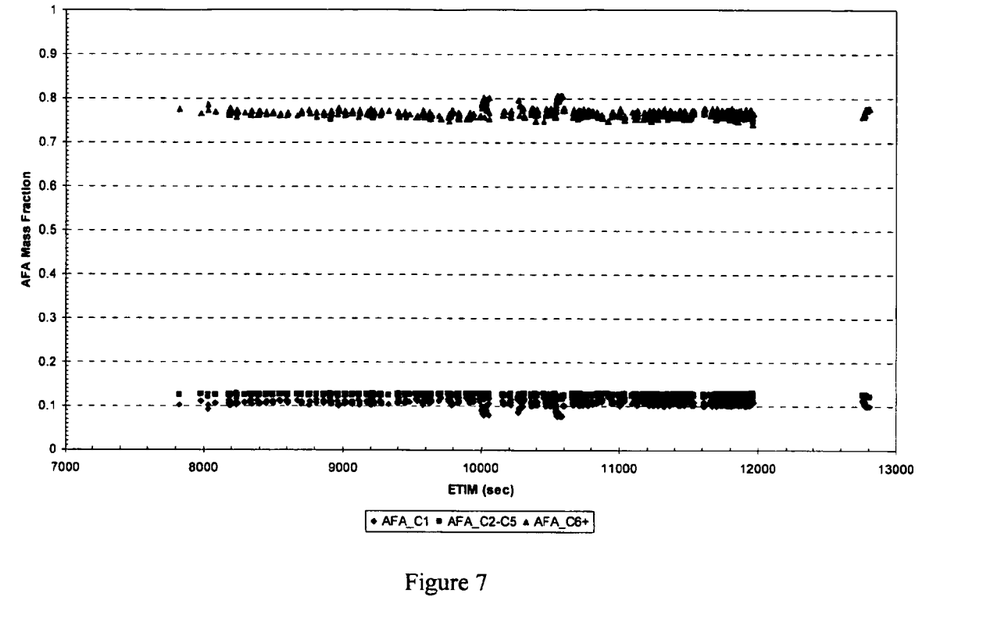
FIG. 7 is a diagram used to illustrate an example of the result of the present method to indicate the C1, C2-C5 and C6+ mass fractions of oil.
Figure 8:
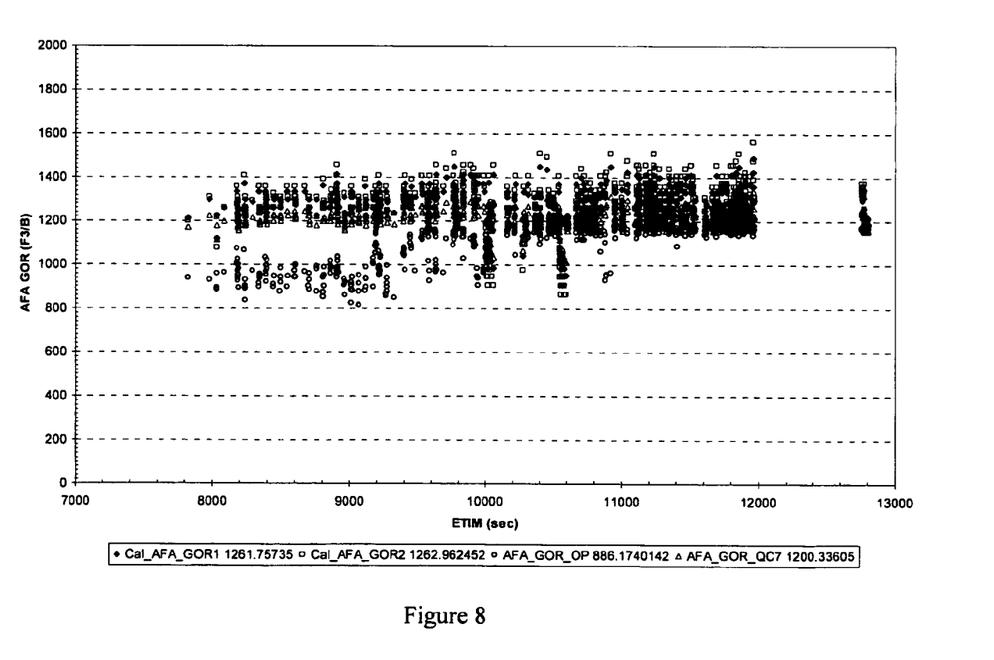
FIG. 8 is a diagram used to illustrate another example of the result of the present method to indicate the agreement between GOR computed using the present method and the conventionally computed GOR.

FIG. 7 shows the computed C1, C2-C5, and C6+ mass fractions of oil according to the present invention, and FIG. 8 shows the agreement between the conventionally computed AFA GOR and the values (Cal_AFA_GOR1, Cal_AFA_GOR2, AFA_GOR_QC7) computed from equation (18), (19) and (22). The lab analysis showed GOR of 1250 scf/stb.

(3) LFA Example

Figure 9:
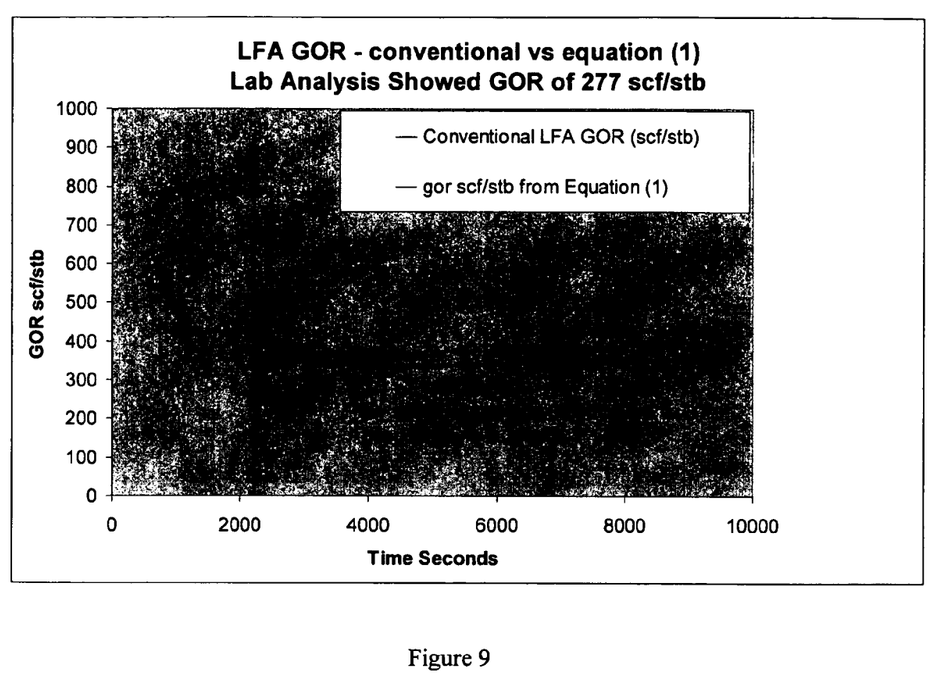
FIG. 9 is a diagram used to illustrate still another example of the result of the present method to indicate the agreement between the GOR computed using the present method and the conventionally computed GOR.

FIG. 9 shows the agreement between the conventionally computed LFA GOR and the values computed from equation (22), where oil_specific_gravity is determined from the lab experiments, and gas_resevoir_density was calculated from the lab compositions of the flash gas.

(4) OFA Example

Figure 10:
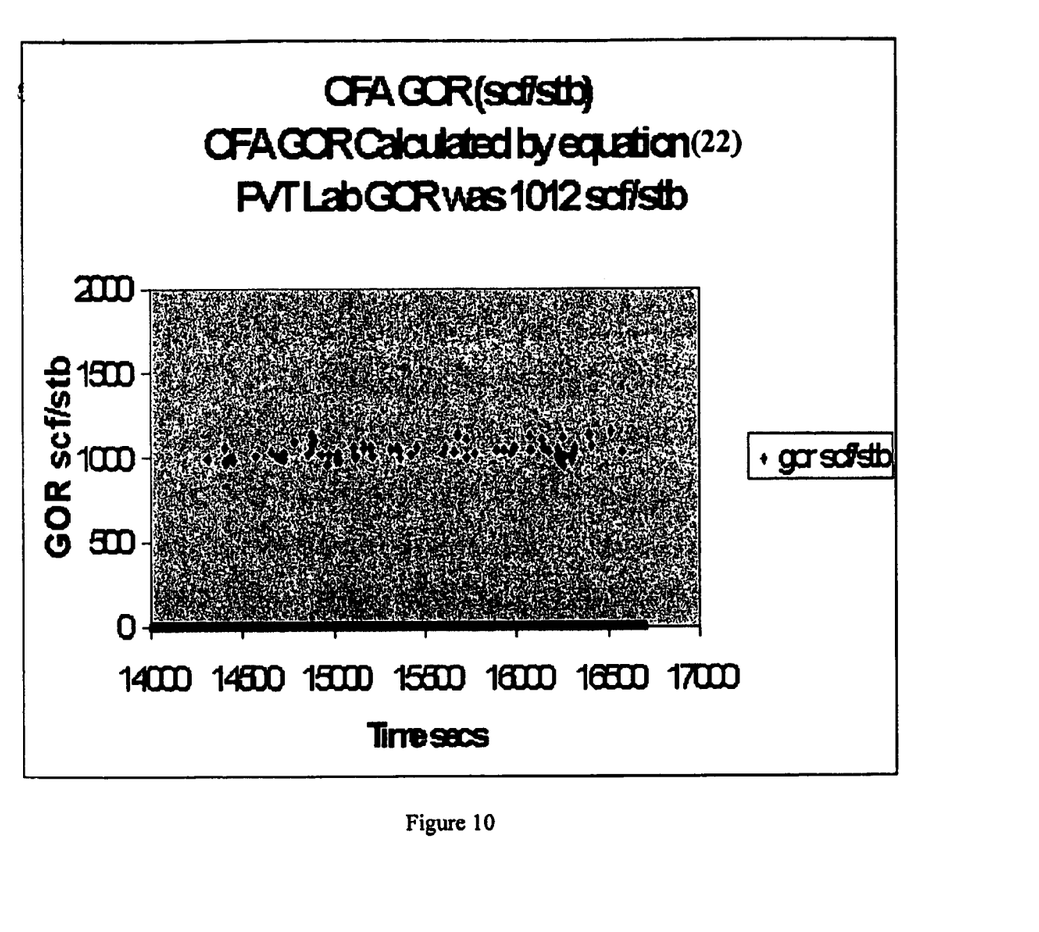
FIG. 10 is a diagram used to illustrate still another example of the result of the present method to indicate the GOR computed using the present method.

FIG. 10 shows the OFA GOR computed for a well in Abu Dhabi by equation (22), where the PVT laboratory GOR was 1012 scf/stb.

(5) LFA Example

Figure 11:
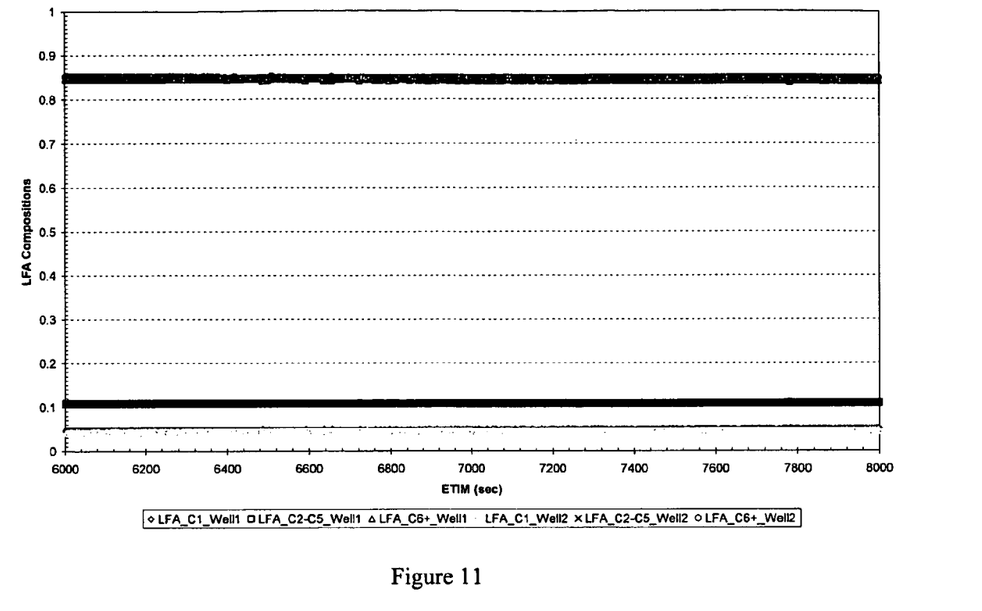
FIG. 11 is a diagram used to illustrate still another example of the result of the present method to indicate the agreement between the results of the present methods to compute compositions from two wells.
Figure 12:
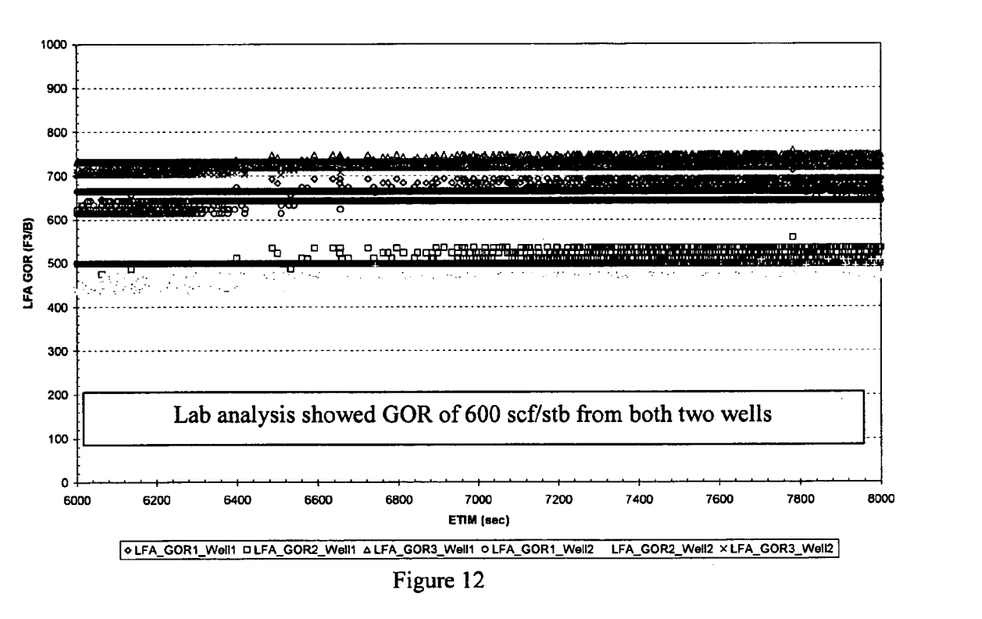
FIG. 12 is a diagram used to illustrate still another example of the result of the present method to indicate the agreement between the results of the present methods to compute GOR from two wells.

Two measurements performed in two wells by a same LFA, at almost identical TVD sub-sea in a same oil zone. Ideally, this LFA should give identical answers. However, our experiment shows that two conventionally computed GOR from the two wells by this LFA were 200 scf/stb and 1320 scf/stb respectively. FIG. 11 shows the agreements between the computed C1, C2-C5, and C6+ mass fractions of by using the linear fit of correlation (equation (6) to (8)) from these two wells. FIG. 12 shows the agreements between the computed GORs (LFA_GOR1, LFA_GOR2, LFA_GOR3) from equations (18), (19), and (22) from these two wells. The variations of computed GORs are from 470 scf/stb to 730 scf/stb, comparing to the variations of conventional GOR from 200 scf/stb to 1320 scf/stb. FIG. 12 also shows the GOR determined from the PVT laboratory experiments.

Certain embodiments of the present invention may present one or more of the following advantages. The embodiments of the present invention enable the determination of compositions (C1, C2-C5, and C6+) of liquid hydrocarbon and GOR based on fluid data related to Carbon-Hydrogen molecular bonds in C6+, without using the measurement of the absorptions by the molecular bonds of methane. Therefore, the in-situ composition analysis capability of the fluid analyzer OFA, LFA and AFA is exploited. Further, alternative methods of determining GOR are available to provide an independent quality check on the conventionally computed GOR which is very sensitive to the small drift of the measurement of the absorptions by the molecular bonds of methane. Finally, certain embodiments of the present invention are able to provide an extra capability to determine compositions (C1, C2-C5, and C6+) and GOR of low GOR (e.g., <400 scf/stb) oil.

The foregoing description of the preferred and alternate embodiments of the present invention has been presented for purposes of illustration and description. It is not intended to be exhaustive or limit the invention to the precise examples described. Many modifications and variations will be apparent to those skilled in the art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the accompanying claims and their equivalents.

We claim:

1. A method for determining properties of a formation fluid, comprising:
   a) obtaining a first fluid data related to Carbon-Hydrogen molecular bonds in C6+ from a fluid analyzer;
   b) obtaining a second fluid data related to Oxygen-Hydrogen bonds of water molecules from the fluid analyzer; and
   c) considering said first and second fluid data to calculate mass fractions of hydrocarbon flowing through the fluid analyzer.

2. The method of claim 1, wherein said considering said fluid data is based on assumption that the total hydrocarbon fraction from the fluid analyzer at a specific time is 1.0 in case of the absence of water in the flowline.

3. The method of claim 1, wherein said considering said fluid data is based on assumption that the total fraction of hydrocarbon/water mixture at a specific time is 1.0 in case of oil and water mixing flow in the flowline.

4. The method of claim 1, wherein the mass fractions of hydrocarbon are C1-C5 and C6+ mass fractions.

5. The method of claim 1 further comprising deriving a correlation related to said mass fractions of hydrocarbon.

6. The method of claim 1 further comprising computing gas-oil-ratio of hydrocarbon based on said mass fractions of hydrocarbon.

7. The method of claim 6, wherein said computing gas-oil-ratio is based on assumption that the non-water formation fluid has negligible amounts molecular bonds that are not Carbon-Hydrogen, where compounds that contain such negligible amounts molecular bonds are N2, H2S, CO2 and asphaltenes.

8. The method of claim 1, wherein the fluid analyzer is Optical Fluid Analyzer, Live Fluid Analyzer, or Advanced Fluid Analyzer.

9. A fluid analyzer comprising:
   a) a sensor for measuring fluid data related to Carbon-Hydrogen molecular bonds in C6+ and further measuring fluid data related to Oxygen-Hydrogen bonds of water molecules; and
   b) a processor for calculating mass fractions of hydrocarbon flowing through the fluid analyzer based on the measured fluid data.

10. The fluid analyzer of claim 9, wherein the mass fractions of hydrocarbon are C1-C5 and C6+ mass fractions.

11. The fluid analyzer of claim 9, wherein the processor further computes gas-oil-ratio of hydrocarbon based on said mass fractions of hydrocarbon.

12. A method for determining a gas-oil-ratio of a formation fluid, comprising:
   a) obtaining a first fluid data related to Carbon-Hydrogen molecular bonds in C6+ and a second fluid data related to Oxygen-Hydrogen bonds of water molecules from a fluid analyzer;
   b) considering said first and second fluid data to derive mass fractions of gas and oil; and
   c) computing gas-oil-ratio of hydrocarbon based on said derived mass fractions.

13. The method of claim 12, wherein said computing gas-oil-ratio is based on assumption that the non-water formation fluid has negligible amounts molecular bonds that are not Carbon-Hydrogen, where compounds that contain such negligible amounts molecular bonds are N2, H2S, CO2 and asphaltenes.

14. The method of claim 12, wherein the fluid analyzer is Optical Fluid Analyzer, Live Fluid Analyzer, or Advanced Fluid Analyzer.

* * * * *